United States Patent [19]

Iwanami et al.

[11] E Patent Number: Re. 33,778

[45] Reissued Date of Patent: Dec. 24, 1991

[54] 1,3-DITHIETANE-2-CARBOXYLIC ACID PENICILLIN AND CEPHALOSPORIN DERIVATIVES

[75] Inventors: Masaru Iwanami, Yokohama; Tetsuya Maeda, Urawa; Yoshinobu Nagano, Niiza; Masaharu Fujimoto, Tokyo; Noriaki Nagano, Ageo; Atsuki Yamazaki, Ichikawa; Kazaharu Tamazawa, Minamisaitama; Kiyoshi Murase, Urawa; Tadao Shibanuma, Asaka, all of Japan

[73] Assignee: Yamanouchi Pharmaceutical Co., Ltd., Tokyo, Japan

[21] Appl. No.: 449,114

[22] Filed: Dec. 8, 1989

Related U.S. Patent Documents

Reissue of:

[64] Patent No.: 4,414,153
Issued: Nov. 8, 1983
Appl. No.: 304,986
Filed: Sep. 23, 1981

U.S. Applications:

[60] Continuation of Ser. No. 294,914, Jan. 6, 1989, abandoned, which is a continuation of Ser. No. 105,464, Oct. 2, 1987, abandoned, which is a continuation of Ser. No. 731,839, May 8, 1985, abandoned, which is a continuation of Ser. No. 48,015, Jun. 13, 1979, abandoned, which is a division of Ser. No. 913,501, Jun. 7, 1978, Pat. No. 4,198,339.

[30] Foreign Application Priority Data

| | | | |
|---|---|---|---|
| Jul. 28, 1977 | [JP] | Japan | 52-90772 |
| Feb. 2, 1978 | [JP] | Japan | 53-10772 |
| Feb. 22, 1978 | [JP] | Japan | 53-19512 |

[51] Int. Cl.[5] ..... C07D 501/36; C07D 499/76

[52] U.S. Cl. ..... 540/222; 540/221; 540/227; 540/228; 540/314; 540/316; 540/327; 546/284; 548/142; 548/187; 548/213; 548/229; 548/251; 548/255; 549/59; 549/89

[58] Field of Search ..... 540/314, 327, 222, 228, 540/221, 227

[56] References Cited

U.S. PATENT DOCUMENTS

| | | | |
|---|---|---|---|
| 3,775,299 | 8/1973 | Weisbach | 540/314 |
| 4,001,218 | 1/1977 | Schmidt et al. | 540/314 |
| 4,263,432 | 4/1981 | Iwanami et al. | 544/21 |

*Primary Examiner*—Jose G. Dees
*Assistant Examiner*—Vera C. Clarke
*Attorney, Agent, or Firm*—Burgess, Ryan & Wayne

[57] ABSTRACT

Substituted 1,3-dithietane-2-carboxylic acid derivatives useful as intermediates for the preparation of highly effective penicillin and cephalosporin derivatives and the preparation thereof.

7 Claims, No Drawings

1,3-DITHIETANE-2-CARBOXYLIC ACID PENICILLIN AND CEPHALOSPORIN DERIVATIVES

Matter enclosed in heavy brackets [ ] appears in the original patent but forms no part of this reissue specification; matter printed in italics indicates the additions made by reissue.

CROSS-REFERENCE TO RELATED APPLICATIONS

*This reissue application is a continuation of reissue application Ser. No. 294,914, filed Jan. 6, 1989, now abandoned, which is a continuation of reissue application Ser. No. 105,464, filed Oct. 2, 1987, now abandoned, and which, in turn, is a continuation of reissue application Ser. No. 731,839, filed May 8, 1985, now abandoned.*

[This application] *U.S. Pat. No. 4,414,153* is a continuation of co-pending application Ser. No. 48,015, filed June 13, 1979, now abandoned which, in turn, is a division of application Ser. No. 913,501, filed June 7, 1978, now U.S. Pat. No. 4,198,339.

DETAILED EXPLANATION OF THE INVENTION

This invention relates to novel compounds. More particularly, the invention relates to novel compounds which are useful as intermediates in the production of therapeutically active penicillin and cephalosporin derivatives, and to the processes for preparing these compounds.

It is an object of this invention to provide a new class of chemical intermediates which can be easily converted to penicillins and cephalosporins as well as other therapeutically useful substances.

It is another object of this invention to provide a process for the preparation of the novel compounds.

Various investigations have already been made about the acyl groups to be introduced to the amino group at the 6-position or 7-position of penicillin or cephalosporin. Some of these investigations disclose heterocyclic compounds. For example, U.S. Pat. No. 3,271,407 discloses isothiazolylacetic acid.

Also, as an example of heterocyclic acetic acids having introduced thereto a cephalosporin ring, 1,3-dithiol-2-one-4-ylacetic acid is known (see, U.S. Pat. No. 4,034,090; U.K. Pat. No. 1,468,102; DT 2,529,300; and French Pat. Nos. 2,322,548 and 2,311,549).

However, since the 1,3-dithietane-2-carboxylic acid having a 1,3-dithietane ring which is a 4-membered ring of two sulfur atoms having a carboxyl group directly bonded to the heterocyclic ring is a novel compound, the carboxylic acid forms as a matter of course a novel acyl group which has never been introduced in the amino group of penicillin or cephalosporin.

The compounds of the present invention are represented by formula I

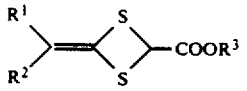

I wherein $R^1$ represents a carboxyl group or the functional derivative residue which may be substituted; $R^2$ represents a carboxyl group or the functional derivative residue thereof which may be substituted, a hydrogen atom, a substituted or unsubstituted lower alkyl group, a lower alkoxy group, a lower alkanoyl group, $R^4S(O)_n$ group (wherein $R^4$ represents a lower alkyl group and n represents 0, 1 or 2), a substituted or unsubstituted aryl group, an aroyl group, a lower alkenyl group, a sulfamoyl group, or a substituted or unsubstituted heterocyclic residue; and $R^3$ represents a hydrogen atom or a lower alkyl group.

The functional derivative residues of carboxyl group in this invention represent, for example, carboxylic acid lower alkyl ester residues, carboxylic acid aralkyl ester residues, a carbamoyl group, a carbazoyl group, a cyano group, etc. The lower alkyl group in this invention is a straight or branched chain alkyl group having 1–4 carbon atoms, such as a methyl group, ethyl group, isopropyl group, n-butyl group, tert-butyl group, etc. Examples of the aryl group are the phenyl group, naphthyl group, etc. Examples of the aroyl group are the benzoyl group, naphthoyl group, etc. As the heterocyclic compounds constituting the heterocyclic residues, there are 5-membered and 6-membered ring compounds having carbon atoms, and an oxygen atom, sulfur atom, and/or nitrogen atom as the hetero atom or atoms, such as the pyrrole ring pyridine ring, pyrimidine ring, thiazole ring, isothiazole ring, oxazole ring, pyridazine ring, thiadiazole ring, oxadiazole ring, triazole ring, tetrazole ring, furan ring, thiophene ring, pyran ring, thiopyran ring, etc.

Examples of the lower alkenyl group are the vinyl group, allyl group, 1-propenyl group, isopropenyl group, etc.

Furthermore, the residues represented by $R^1$, $R^2$, $R^3$ and $R^4$ can have a substituent, and such a substituent includes, for example, a hydroxyalkyl group, alkoxyalkyl group, carboxyalkyl group, arylalkyl group, hydroxyphenyl group, alkoxyphenyl group, N-monoalkylcarbamoyl group, N,N-dialkylcarbamoyl group, hydroxypyridyl group, methylpyridyl group, alkylthiothiadiazolyl group, etc.

The compounds of this invention are prepared by reacting, for example, the ethylene-1,1-dithiol represented by general formula II

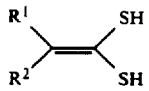

II wherein $R^1$ and $R^2$ have the same significance as in general formula I and the dihalogenoacetic acid or lower alkyl ester thereof represented by general formula III

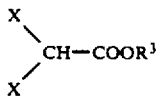

III wherein X represents a halogen atom and $R^3$ has the same significance as in general formula I.

It is preferred to perform the reaction using the compound of formula II and an equimolar or excessive molar amount of the compound of formula III in a solvent which does not affect the reaction in the presence of a base under cooling or under heating.

Examples of the solvent used in this reaction are methanol, ethanol, butanol, methylene chloride, tetrahydrofuran, benzene, toluene, dimethoxyethane, anisole, acetone, dimethylsulfoxide, dimethylformamide, dimethylaniline, etc., and examples of the base used in this reaction are pyridine, triethylamine, dicyclohexylamine, an alkali metal (e.g., metallic potassium, etc.,), an alkali metal hydride (e.g., sodium hydride, potassium hydride, etc.,), an alkyl lithium (e.g., methyl lithium, tert-butyl lithium, etc.,), sodium carbonate, potassium carbonate, lithium diisopropylamine, etc.

The preferred halogen atom of the compound of formula III is a chlorine atom, a bromine atom, or an iodine atom. Also, when $R^3$ of general formula III is a hydrogen atom, the alkali metal salt of the compound, such as the sodium salt, potassium salt, etc., of the compound can be used for the reaction.

When $R^3$ of general formula I is a lower alkyl group, the compound of the formula I can be converted to the compound of formula I wherein $R^3$ is a hydrogen atom by decomposing the compound in the aforesaid organic solvent in the presence of an acid such as hydrochloric acid, acetic acid, trifluoroacetic acid, etc.

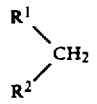

IV wherein $R^1$ and $R^2$ have the same significance as in general formula I and carbon disulfide in the organic solvent described above in the presence of the aforesaid base under cooling or heating.

The compound of formula I thus obtained can be introduced to the amino group of the penicillin or cephalosporin by conventional methods by forming an acid amide with the amino group at the 6-position of the penicillin ring or the 7-position of the cephalosporin ring and thus useful antibiotics can be produced.

Then, examples of the compounds obtained using the compounds of this invention shown by formula I as the starting material are illustrated together with antibiotic activity below, whereby it becomes apparent that the compounds of this invention are useful compounds.

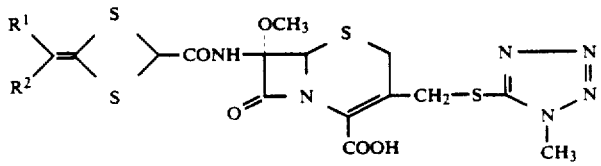

| Compound | $R^1$ | $R^2$ | *Escherichia Coli* NIHJ | *Klebsiella pneumoniae* ATCC 10031 | *Proteus vulgaris* OXK US | *Proteus morganii* Kono | *Serratia marcescens* |
|---|---|---|---|---|---|---|---|
| 1 | HOOC— | $CH_3$— | 0.09 | 0.09 | 0.78 | 1.56 | 0.78 |
| 2 | " | H— | 0.19 | 0.19 | 1.56 | 1.56 | 0.78 |
| 3 | " | 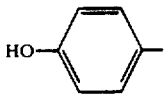 | 0.39 | 0.39 | 0.78 | 6.25 | 6.25 |
| 4 | " | 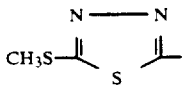 | 6.25 | 3.13 | 1.56 | 50 | 50 |
| 5 | " | $C_2H_5S$— | 0.19 | | 0.39 | 0.78 | 0.78 |
| 6 | " | $CH_3SO_2$— | 0.19 | 0.19 | 1.56 | 3.13 | 0.78 |
| 7 | $H_2NOC$— | NC— | 0.78 | 0.39 | 0.78 | | |
| 8 | HOOC— | $H_2NO_2S$— | 0.19 | 0.19 | 1.56 | 3.13 | 0.78 |
| 9 | " | 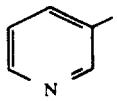 | 0.78 | 0.39 | 0.78 | 3.13 | 3.13 |
| 10 | $CH_3NHOC$— | HOOC— | 0.78 | 0.39 | 1.56 | 1.56 | 0.78 |

These compounds were produced by the similar procedure as in Reference examples 1 and 2.

Also, when $R^1$ and/or $R^2$ of general formula I is a carbamoyl group, the compound having the carbamoyl group can be converted to the compound having a cyano group by performing the dehydration reaction thereof in the aforesaid organic solvent in the presence of, for example, phosphorus oxychloride, phosphorus pentachloride, thionyl chloride, sulfuryl chloride, etc.

The compounds of formula II used as the raw material in this invention include known materials as well as novel compounds and can be prepared by reacting the compound shown by general formula IV

REFERENCE EXAMPLE 1

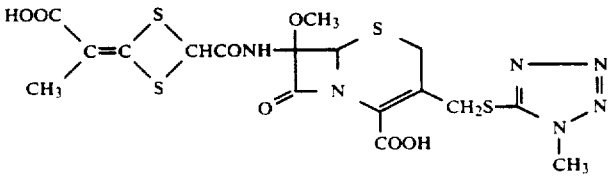

(a). In 15 ml. of methylene chloride were dissolved 0.340 g. of 4-[1-(tert-butoxycarbonyl)ethylidene]-1,3-dithietane-2-carboxylic acid and 0.206 g. of pyridine. While stirring the solution in an ice-water bath, 0.284 g. of phosphorus pentachloride was added to the solution. The reaction was carried out for one hour at a temperature below 10° C. and then after cooling the reaction mixture to −50° C., a solution of 0.690 g. of 7β-amino-7α-methoxy-3-(1-methyltetrazol-5-yl)thiomethyl-$\Delta^3$-cephem-4-carboxylic acid benzhydryl ester in 10 ml. of methylene chloride was added dropwise to the solution and then 1.6 ml. of pyridine was added dropwise and the mixture was caused to react for one hour at temperatures of from −30° C. to −40° C.

After the reaction was over, 10 ml. of 5 normal hydrochloric acid was added dropwise to the reaction mixture below 0° C. and the product was extracted with methylene chloride. The extract was washed with a saturated aqueous sodium chloride solution, dried over anhydrous calcium chloride, and then methylene chloride was distilled off to provide 1.1 g. of a residue. The residue was subjected to a silica gel column chromatography and then 0.490 g. (yield 47%) of caramel-like 7β-{1-[1-(tert-butoxycarbonyl)ethylidene]-1,3-dithietan-2-yl]carboxamido-7α-methoxy-3-(1-methyltetrazol-5-yl)thiomethyl-cephem-4-carboxylic acid benzhydryl ester was obtained using a mixture of ethyl acetate and n-hexane of 1:1 by volume ratio as the eluent.

Nuclear magnetic resonance spectra ($D_6$-DMSO)

δ(p.p.m.): 1.44 (9H, tert-butyl), 1.56 (3H, 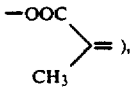 ), 3.49 (3H, ---$OCH_3$), 3.90 (3H, 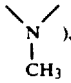 ), 5.10 (1H), 5.15 (1H) } H of $C_6$ and 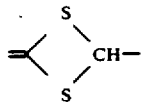

6.92 (1H, —$CH(C_6H_5)_2$),
9.68 (1H, —CONH—).

(b). In 25 ml. of anisole was dissolved 0.44 g. of the product obtained in step (a) and while cooling the solution below 5° C. with ice-water, 7.5 ml. of trifluoroacetic acid was added dropwise to the solution. The reaction was performed for one hour at 5°-10° C., anisole and excess trifluoroacetic acid were distilled off under reduced pressure, and the residue was powdered by adding thereto ether. After recovering the powder by filtration, the powder was washed well with ether to provide 0.271 g. (yield 86.7%) of the light yellow powder of 7β-[4-(1-carboxyethylidene)-1,3-dithietan-2-yl]carboxamido-7α-methoxy-3-(1-methyltetrazol-5-yl)thiomethyl-$\Delta^3$-cephem-4-carboxylic acid.

Nuclear magnetic resonance spectra ($D_6$-DMSO)

δ(p.p.m.): 1.56 (3H, 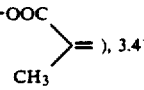 ), 3.41 (3H, ---$OCH_3$), 3.93 (3H, 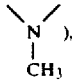 ), 5.13 (2H) H of $C_6$ and 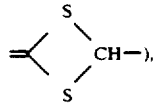

9.57 (1H, —CONH—)
Infrared spectrum (KBr)($cm^{-1}$)
1870 (lactam).

REFERENCE EXAMPLE 2

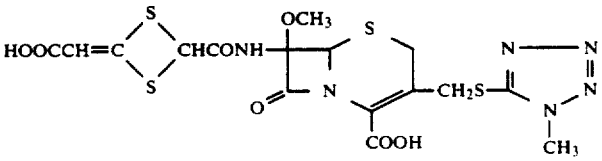

(a). In 20 ml. of methylene chloride was dissolved 0.714 g. of 4-(tert-butoxycarbonylmethylene)-1,3-dithietane-2-carboxylic acid. Then 0.454 g. of pyridine was added to the solution followed by cooling to a temperature below 5° C. Thereafter, 0.630 g. of phosphorus pentachloride was added to the mixture to cause the reaction for one hour at a temperature below 10° C. The reaction mixture obtained was cooled to about −50° C. and a solution prepared by dissolving 1.5 g. of 7β-amino-7α-methoxy-3-(1-methyltetrazol-5-yl)-thiomethyl-$\Delta^3$-cephem-4-carboxylic acid benzhydryl ester in 15 ml. of methylene chloride was added dropwise to the reaction mixture. Then, 3 ml. of pyridine was added and the reaction was performed for 1 hour at −30° C. to −35° C. After the reaction was over, 20 ml. of 6 normal hydrochloric acid was added to the reaction mixture at a temperature below 0° C. The methylene chloride layer formed was recovered and the aqueous layer was further extracted with 20 ml. of methylene chloride. The extract was combined with the methylene chloride layer and the mixture was washed twice, each time with 20 ml. of a saturated aqueous sodium chloride solution, dried over anhydrous magnesium sulfate, and then the solvent was distilled off to provide 1.89 g. of a brown caramel residue. The residue was subjected to a silica gel column chromatography to provide 0.308 g. of 7β-[(4-tert-butoxycarbonylmethylene)-1,3-dithietan-2-yl]carboxamido-7α-methoxy-3-(1-methyltetrazol-5-yl)thiomethyl-$\Delta^3$-cephem-4-carboxylic acid benzhydryl ester using a mixture of ethyl acetate and n-hexane of 2:1 by volume ratio as the eluent.

Nuclear magnetic resonance spectra ($D_6$-DMSO)

δ(p.p.m.): 1.40 (9H, tert-butyl),
3.44 (3H, ---$OCH_3$),

-continued 3.88 (3H, 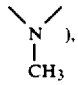 ), 5.23 (1H, H of $C_6$), 5.33 (1H, 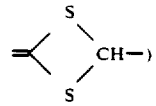 ), 5.84 (1H, 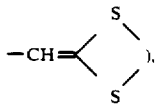 ), 6.88 (1H, $-\underline{CH}(C_6H_5)_2$)
9.66 (1H, —CONH—).

(b). In 1.7 ml. of anisole was dissolved 0.3 g. of the product obtained in aforesaid step (a). After cooling the solution to a temperature below −5° C., 5.1 ml. of trifluoroacetic acid was added dropwise to the solution at a temperature below 0° C. Thereafter, the reaction was performed for 30 minutes at 0°-5° C. and then for 30 minutes at 5°-10° C. After the reaction was over, anisole and trifluoroacetic acid were distilled off under reduced pressure and the residue was powdered with the addition of ether. The powder was washed well with ether, and dried to provide 0.1584 g. of faint-yellow powdery 7β-[4-(carboxymethylene)-1,3-dithietan-2-yl]carboxamido-7α-methoxy-3-(1-methyltetrazol-5-yl)thiomethyl-$\Delta^3$-cephem-4-carboxylic acid.

Nuclear magnetic resonance spectra ($D_6$-DMSO)

δ(p.p.m.): 3.43 (3H, —$OCH_3$), 3.94 (3H, 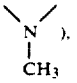 ), 5.17 (1H, H of $C_6$), 5.33 (1H, 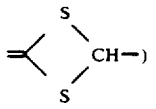 ), 5.84 (1H, 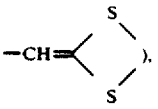 ), 9.63 (1H, —CONH—)

EXAMPLE 1

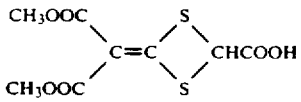

In 10 ml. of anhydrous tetrahydrofuran was suspended 2.1 g. of disodium 2,2-bis(methoxycarbonyl-)ethylene-1,1-dithiolate.

After adding 2.2 g. of sodium dibromoacetate to the suspension, the mixture was stirred for 2 hours at room temperature. The solvent was distilled off from the reaction mixture under reduced pressure and the residue was dissolved in 5 ml. of water. The solution was adjusted to pH 3.5-4.0 with diluted hydrochloric acid and extracted with ethyl acetate. The extract was dried over anhydrous magnesium sulfate and the solvent was distilled off under reduced pressure. The residue was mixed with ether and filtered to provide 1.5 g. of 4-[bis(-methoxycarbonyl)methylene]-1,3-dithietane-2-carboxylic acid.

Nuclear magnetic resonance spectra ($D_6$-DMSO)

δ(p.p.m.): 3.70 (6H, 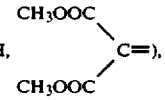 ), 5.20 (1H, 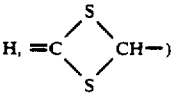 )

EXAMPLE 2

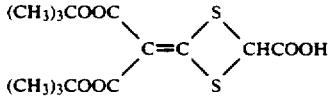

By following the same procedure as in Example 1 using disodium 2,2-bis(tert-butoxycarbonyl)ethylene-1,1-dithiolate, 4-[bis(tert-butoxycarbonyl)methylene]-1,3-dithietane-2-carboxylic acid was obtained.

Nuclear magnetic resonance spectra ($D_6$-DMSO)

δ(p.p.m.): 1.46 (9H, $(CH_3)_3COOC$—), 5.18 (1H, 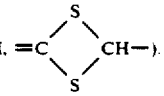 ).

EXAMPLE 3

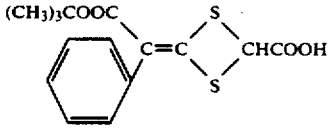

To 15.6 g. of a 15% potassium tert-butylate tert-butanol solution were added 4 g. of tert-butyl phenylacetate and then 1.6 g. of carbon disulfide with stirring at room temperature. After stirring the mixture for 15 minutes, 20 ml. of anhydrous tetrahydrofuran and then 31.2 g. of a 15% potassium tert-butylate tert-butanol solution were added to the mixture and then 2.7 g. of dichloroacetic acid was added dropwise to the mixture at 30°-40° C. followed by stirring for 30 minutes at the same temperature to finish the reaction.

Then, after adding dichloroacetic acid to the reaction mixture until the mixture became weak alkaline, the solvent was distilled off under reduced pressure and the residue was mixed with ice-water followed by washing with ether. Then, 0.5 ml. of 3 normal hydrochloric acid was added to the mixture and the product was extracted with ether. To the extract was further added 0.5 ml. of 3 normal hydrochloric acid. The product was extracted with ether, and the procedure was further repeated. Each extract fraction obtained was detected by a silica gel thin layer chromatography, the fractions containing the objective material were collected and dried over anhydrous magnesium sulfate. Then, the solvent was distilled off under reduced pressure to provide about 1 g. of 4-(α-tert-butoxycarbonylbenzylidene)-1,3-dithietane-2-carboxylic acid.

Nuclear magnetic resonance spectra ($D_6$-DMSO)

δ(p.p.m.): 1.40 (9H, $(CH_3)_3COOC-$), 5.17 (1H, =C(S)(S)CH—), about 7.30 (5H, H—$C_6H_4$—).

EXAMPLE 4

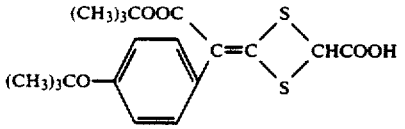

By treating tert-butyl 4-tert-butoxyphenylacetate as in Example 3, 4-(4-tert-butoxy-α-tert-butoxycarbonylbenzylidene)-1,3-dithiethane-2-carboxylic acid was obtained.

Nuclear magnetic resonance spectra ($CDCl_3$)

(p.p.m.): 1.35 (9H), 1.48 (9H) } $(CH_3)_3C-$ 4.85 (1H, =C(S)(S)CH—), 6.93 (2H), 7.15 (2H) } —O—$C_6H_4$—

EXAMPLE 5

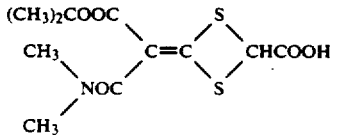

By treating tert-butyl dimethylcarbamoylacetate as in Example 3, 4-[(tert-butoxycarbonyl)(dimethylcarbamoyl)methylene]-1,3-dithietane-2-carboxylic acid was obtained.

Nuclear magnetic resonance spectra ($CDCl_3$)

δ(p.p.m): 1.50 (9H, $(CH_3)_3COOC-$), 3.02 (6H, $(CH_3)_2N-$), 4.97 (1H, =C(S)(S)CH—).

EXAMPLE 6

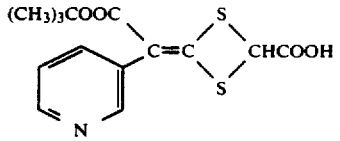

By treating tert-butyl 3-pyridylacetate as in Example 3, 4-[(tert-butoxycarbonyl)(3-pyridyl)methylene]-1,3-dithietane-2-carboxylic acid was obtained.

Nuclear magnetic resonance spectra ($D_6$-DMSO)

δ(p.p.m.): 1.42 (9H, $(CH_3)_3COOC-$), 5.22 (1H, =C(S)(S)CH—), 7.40 (1H), 7.66 (1H), 8.45 (2H) } $C_5H_4N$

EXAMPLE 7

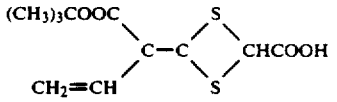

By treating tert-butyl 3-butenoic acid as in Example 3, 4-(1-tert-butoxycarbonyl-2-propene-1-ylidene)-1,3-dithietane-2-carboxylic acid was obtained.

Nuclear magnetic resonance spectra ($CDCl_3$)

δ(p.p.m.): 1.51 (9H, $(CH_3)_3COOC-$),

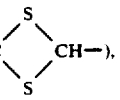

4.98 (1H, =C CH—), 5.00–5.40 (2H, $CH_2=CH-$),
6.10–6.50 (1H, $CH_2=CH-$).

EXAMPLE 8

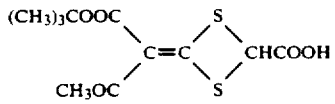

To 150 ml. of tert-butanol was added 4.8 g. of sodium hydride (50% in oil). Then 15.8 g. of tert-butyl acetoacetate was added gradually to the mixture. Then, after adding thereto 7.6 g. of carbon disulfide under ice-cooling, the mixture was stirred for 18 hours at room temperature. Thereafter, 4.8 g. of sodium hydride (50% in oil) was added gradually under ice-cooling and after stirring the mixture for 2 hours at room temperature, 16.7 g of potassium dichloroacetate was added to the mixture followed by stirring for further 2 hours. The reaction mixture obtained was concentrated under reduced pressure. The residue was mixed with 300 ml. of ethyl acetate and 200 ml. of ice-water, and the mixture was adjusted to pH 3–4 with 1 normal hydrochloric acid. The organic layer formed was washed with an aqueous sodium chloride solution, and extracted with a saturated aqueous sodium hydrogencarbonate solution.

The sodium hydrogencarbonate extract was washed with 50 ml. of ethyl acetate, adjusted to pH 3–4 with 1 normal hydrochloric acid, and extracted with 200 ml. of ethyl acetate. The ethyl acetate extract was washed with an aqueous sodium chloride solution, dried over anhydrous sodium sulfate, and then concentrated. The residue was washed with 50 ml. of a mixture of petroleum ether and ether of 10:1 by volume ratio and dissolved in 5 ml. of ether. Then, 50 ml. of petroleum ether was added gradually to the solution and the crystals thus precipitated were recovered by filtration to provide 10 g. of 4-[(acetyl)(tert-butoxycarbonyl)methylene]-1,3-diethietane-2-carboxylic acid.

Nuclear magnetic resonance sepctra ($CDCl_3$)

δ(p.p.m.): 1.53 (9H, $(CH_3)_3COOC-$),
2.49 (3H, $CH_3OC-$),

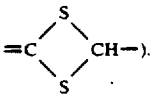

4.94 (1H, =C CH—).

EXAMPLE 9

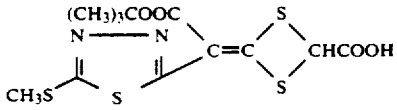

In 100 ml. of tert-butanol was dissolved 1.58 g. of metallic potassium. After adding thereto 10 g. of tert-butyl 5-methylthio-1,3,4-thiadiazole-2-acetate, the mixture was stirred for 20 minutes. Thereafter, 3.25 g. of carbon dilsulfide was added dropwise to the mixture over a period of 10 minutes. After stirring the mixture for one hour, 4.55 g. of potassium tert-butylate was added gradually to the mixture followed by stirring for 20 minutes and then 6.63 g. of potassium dichloroacetate was added to the mixture followed by stirring for 18 hours. The reaction mixture was concentrated under reduced pressure, and the residue was mixed with 300 ml. of ethyl acetate and 200 ml. of ice-water. The mixture was adjusted to pH 3–4 with 1 normal hydrochloric acid, and the organic layer formed was washed with an aqueous sodium chloride solution, and then extracted with 1000 ml. of a saturated aqueous sodium hydrogencarbonate solution. The sodium hydrogencarbonate extract was washed with 100 ml. of ethyl acetate, adjusted to pH 3–4 with 5 normal hydrochloric acid, and then extracted with 200 ml. of ethyl acetate. The ethyl acetate extract was washed with an aqueous sodium chloride solution, dried over anhydrous sodium sulfate, and concentrated. The residue was subjected to a silica gel column chromatography to provide 1 g. of 4-[(tert-butoxycarbonyl)(5-methylthio-1,3,4-thiadiazol-2-yl)methylene)-1,3-dithietane-2-carboxylic acid using chloroform and then a mixture of chloroform and methanol of 50:1 by volume ratio as the eluent.

Nuclear magnetic resonance spectra ($CDCl_3$)

δ(p.p.m.): 1.59 (9H, $(CH_3)_3COOC-$),
2.79 (3H, $CH_3S-$),

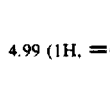

4.99 (1H, =C CH—).

EXAMPLE 10

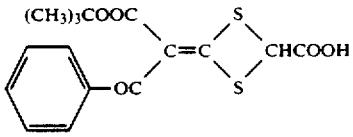

In a mixture of 2.2 g. of tert-butyl benzoylacetate and 20 ml. of tert-butanol was dissolved 0.24 g. of sodium hydride (50% in oil), and 0.6 ml. of carbon disulfide was added to the solution at 15°–20° C. followed by stirring for 40 minutes, and then 0.24 g. of sodium hydride (50% in oil) was added to the mixture followed by stirring for one hour. To the reaction mixture obtained was added 1.52 g. of sodium dichloroacetate followed by stirring for 4 hours at room temperature. The reaction mixture was concentrated under reduced pressure and after adding 30 ml. of 1 normal hydrochloric acid to the residue formed, the product was extracted with 30 ml. of benzene. The extract was washed with water, dried, and concentrated under reduced pressure. By adding a mixture of benzene and n-hexane of 3:1 by volume ratio to the residue formed, 0.9 g. of the yellowish crystals of 4-[(benzoyl)(tert-butoxycarbonyl)methylene]-1,3-dithietane-2-carboxylic acid were obtained.

Melting point: 147°–148° C. (decomposed)

Nuclear magnetic resonance spectra ($CDCl_3$)

δ(p.p.m.): 1.23 (9H, $(CH_3)_3COOC-$), 5.02 (1H, =C 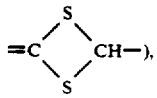 CH—), 7.3–7.5 (5H, H— 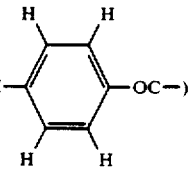 —OC—)

8.22 (1H, —COOH).

EXAMPLE 11

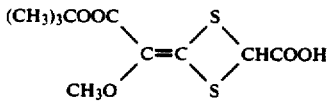

A mixture of 4.5 g. of tert-butyl methoxyacetate and 10 ml. of tetrahydrofuran was added to a lithium diisopropylamine solution prepared by adding 18.2 ml. of a 15% n-butyl lithium hexane solution to a mixture of 3 g. of diisopropylamine and 20 ml. of tetrahydrofuran at temperature of from −40° C. to −70° C. and then after adding thereto 0.9 ml. of carbon disulfide at temperature below −40° C., the resultant mixture was stirred for 20 minutes at the same temperature. Then, after adding to the reaction mixture obtained the lithium diisopropylamine solution of ½ of the aforesaid amount and carbon disulfide of ½ of the aforesaid amount at temperature of from −40° C. to −70° C. to cause reaction, the lithium diisopropylamine solution of ¼ of the aforesaid amount and carbon disulfide of ¼ of the aforesaid amount were further added to the mixture to cause reaction and then 9 g. of sodium diiodoacetate was added to the reaction mixture followed by rising gradually the temperature and stirring for one hour at 0°–5° C. and further for one hour at room temperature. The reaction mixture obtained was concentrated under reduced pressure and after adding 20 ml. of 10% hydrochloric acid to the residue formed, the product was extracted with 100 ml. of benzene. The extract was washed with water and concentrated under reduced pressure. The residue formed was subjected to a silica gel column chromatography and 5.6 g. of 4-[(tert-butoxycarbonyl)(methoxy) methylene]-1,3-dithietane-2-carboxylic acid was obtained using a mixture of chloroform and ethanol of 10:2–5 by volume ratio as the eluent.

Nuclear magnetic resonance spectra ($CDCl_3$)

δ(p.p.m.): 1.52 (9H, $(CH_3)_3COOC-$),
3.67 (3H, $CH_3O-$), 4.88 (1H, =C 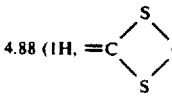 CH—), 8.64 (1H, —COOH).

EXAMPLE 12

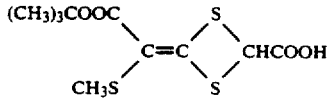

In 14 ml. of anhydrous tetrahydrofuran was suspended 0.96 g. of sodium hydride (50% in oil). After adding dropwise a mixture of 20 ml. of tert-butanol and 15 ml. of anhydrous tetrahydrofuran to the suspension, the mixture was stirred for 10 minutes at room temperature. Then, to the mixture was added a mixture of 1.62 g. of tert-butyl methylthioacetate and 5 ml. of anhydrous tetrahydrofuran at 3°–5° C. and after 30 minutes, 0.6 ml. of carbon disulfide was added to the mixture at the same temperature followed by stirring for 50 minutes. Then, 3.34 g. of sodium diiodoacetate was added to the mixture at temperature below 7° C. and they were caused to react for 50 minutes under ice-cooling. The solvent was distilled off under reduced pressure, the residue formed was dissolved in 50 ml. of ice-water, and the solution was washed twice each time with ether. The aqueous layer formed was recovered, adjusted to pH 2 with 10% hydrochloric acid, dried over anhydrous magnesium sulfate, and then ether was distilled off under reduced pressure. The residue was subjected to a silica gel column chromatography and 1.3 g. of oily 4-[(tertbutoxycarbonyl)(methylthio)methylene]-1,3-dithietane-2-carboxylic acid using a mixture of chloroform, methanol, and formic acid by volume ratio as the eluent.

Nuclear magnetic resonance spectra ($CDCl_3$)

δ(p.p.m.): 1.52 (9H, $(CH_3)_3COOC-$),
2.22 (3H, $CH_3S-$), 4.74 (1H, =C 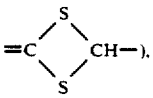 CH—), 9.12 (1H, —COOH).

EXAMPLE 13

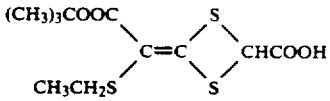

By treating 3.4 g. of tert-butyl ethylthioacetate as in Example 12, 4.05 g. of oily 4-[(tert-butoxycarbonyl)(ethylthio)methylene]-1,3-dithietane-2-carboxylic acid was obtained.

Nuclear magnetic resonance spectra ($CDCl_3$)

δ(p.p.m.): 1.42 (3H, $CH_3CH_2S-$),
1.52 (9H, $(CH_3)_3COOC-$),
2.68 (2H, $CH_3CH_2S-$), 4.76 (1H, =C 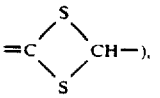 CH—), -continued

| |
|---|
| 9.52 (1H, —COOH). |

EXAMPLE 14

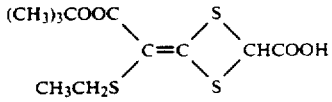

In a mixture of dimethoxyethane and 10 ml. of tetrahydrofuran both were deoxygenated by distillation were added 1 ml. of n-isopropylcyclohexylamine and 3.43 ml. of a 15% n-butyl lithium n-hexane solution under cooling below −70° C. Then, after adding thereto 0.65 g. of tert-butyl propionate, the mixture was stirred for about 30 minutes at temperatures below −70° C. To the reaction mixture was added dropwise 0.332 ml. of carbon disulfide at temperatures of from −75° C. to −73° C. over a period of about 30 minutes. The reaction was further carried out for 10 minutes at temperature below −70° C. and then 3.4 ml. of a 15% n-butyl lithium n-hexane solution was added dropwise to the reaction mixture at temperature below −70° C. over a period of about 30 minutes. After carrying out the reaction for 15 minutes at temperature below −70° C., sodium diiodoacetate obtained beforehand by reacting 0.24 g. of 50% oily sodium hydride and 1.56 g. of diiodoacetic acid in 10 ml. of dimethoxyethane under ice-cooling was added to the reaction mixture and the mixture was stirred overnight at room temperature.

The solvent was distilled off from the reaction mixture under reduced pressure and after adding cold ether to the residue and acidifying the residue with 1 normal hydrochloric acid, the product was extracted with ether. The ether extract was washed well with a saturated aqueous sodium chloride solution, dried over anhydrous magnesium sulfate, and then the ether was distilled off to provide 1.42 g. of a brown oily product. The product was subjected to silica gel column chromatography and 0.5 g. of oily 4-[(1-(tert-butoxycarbonyl)ethylidene]-1,3-dithietane-2-carboxylic acid was obtained using a mixture of chloroform, methanol, and formic acid of 95:5:2 by volume ratio as the eluent.

Nuclear magnetic resonance spectra ($D_6$-DMSO)

| | |
|---|---|
| δ(p.p.m.): | 1.42 (9H, tert-butyl) |
| | 1.53 (3H, 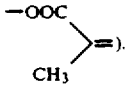 ). |
| | 5.14 (1H, 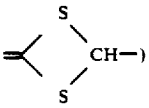 ) |
| Infrared spectra ($cm^{-1}$): | |
| | 2970 (tert-butyl), |
| | 2520–2650 (—COOH), |
| | 1640–1740 (—COO-tert-butyl, —COOH), |
| | 1360, 1250, and 840 (tert-butyl) |

EXAMPLE 15

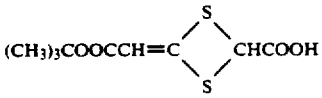

A mixture of 80 ml. of dimethoxyethane and 20 ml. of tetrahydrofuran both were deoxygenated by distillation was cooled below −70° C. in a nitrogen stream and after adding thereto 2 ml. of N-isopropyl cyclohexylamine and 6.86 ml. of a 15% n-butyl lithium n-hexane solution, 1.16 g. of tert-butyl acetate was added dropwise to the mixture. Then, the reaction was performed for 30 minutes at a temperature below −70° C. and then 0.664 ml. of carbon disulfide was added to the reaction mixture over a period of about 30 minutes at a temperature below −72° C. The reaction mixture colored light yellow. After further causing the reaction for 20 minutes at a temperature below −70° C., 6.8 ml. of 15% n-butyl lithium n-hexane solution was added dropwise to the reaction mixture over a period of 15 minutes at a temperature below −72° C. Thereafter, the reaction was further performed for 20 minutes at a temperature below −70° C. and then a solution containing crystals of sodium diiodoacetate prepared from 0.48 g. of 50% sodium hydride and 3.12 g. of diiodacetic acid in 15 ml. of dimethoxyethane was added to the reaction mixture. The temperature of the reaction mixture was allowed to raise to room temperature and the reaction mixture was further reacted overnight. The solvent was distilled off and the black-brown oily material obtained was extracted with the additions of 50 ml. of cold ether and 20 ml. of 1 normal hydrochloric acid.

The aqueous layer was further extracted with the addition of 30 ml. of cold ether and the extracts were combined. The mixture was washed twice, each time with 30 ml. of a saturated aqueous sodium chloride solution, dried over anhydrous magnesium sulfate, and then ether was distilled off to provide 3 g. of a brown oily product. The product was subjected to a silica gel column chromatography to provide 0.564 g. of 4-(tert-butoxycarbonylmethylene)-1,3-dithietane-2-carboxylic acid using a mixture of chloroform, methanol, and formic acid of 95:5:2 by volume ratio as the eluent.

Nuclear magnetic resonance spectra ($D_6$-DMSO)

| | |
|---|---|
| δ(p.p.m.): | 1.45 (9H, tert-butyl), |
| | 5.03 (1H, 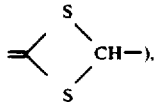 ), |
| | 5.69 (1H, 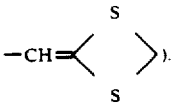 ). |

EXAMPLE 16

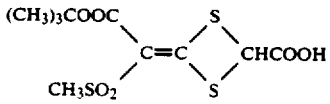

In 65 ml. of tert-butanol was dissolved 2.05 g. of tertbutyl methylsulfonylacetate. After adding thereto 1.32 g. of potassium tert-butylate, the mixture was stirred for 5 minutes. After adding dropwise 0.91 g. of carbon disulfide to the mixture and stirring them for 5 minutes, 1.32 g. of potassium tert-butylate was added to the mixture followed by stirring for one hour Then, 3.8 g. of diiodoacetic acid and 1.32 g. of potassium tert-butylate were added to the mixture and the resultant mixture was stirred overnight. The solvent was distilled off from the reaction mixture obtained under reduced pressure. The residue formed was mixed with water, adjusted to pH 2 with 10% hydrochloric acid, and extracted with ethyl acetate. The extract was washed with water and then a saturated aqueous sodium chloride solution, dried over anhydrous magnesium sulfate, and then the solvent was distilled off under reduced pressure. The residue was subjected to a silica gel column chromatography to provide 1.7 g. of 4-[(tertbutoxycarbonyl)(methylsulfonyl)methylene]-1,3-dithietane-2-carboxylic acid using a mixture of chloroform and methanol of 50:1 by volume ratio as the eluent.

Nuclear magnetic resonance spectra ($CDCl_3$)

| | |
|---|---|
| δ(p.p.m.): | 1.52 (9H, $(CH_3)_3COOC-$)<br>3.20 (3H, $CH_3SO_2-$),<br>4.88 (1H, =C 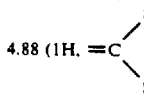 CH—). |

EXAMPLE 17

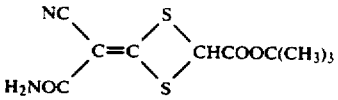

In 50 ml. of dimethyl sulfoxide was dissolved 4.8 g. of disodium 2-carbamoyl-2-cyano-ethylene-1,1-dithiolate. After adding 6.28 g. of tert-butyl dibromoacetate to the solution, the mixture was stirred for 48 hours at room temperature. The solvent was distilled off from the reaction mixture obtained under reduced pressure and the product was extracted with ethyl acetate. The extract was washed with water and then an aqueous sodium chloride solution, dried over anhydrous magnesium sulfate, and then the solvent was distilled off under reduced pressure. The residue was subjected to a silica gel column chromatography and 0.8 g. of tert-butyl 4-[(carbamoyl)(cyano)methylene]-1,3-dithietane-2-carboxylate using a mixture of chloroform and ethyl acetate of 7:1 by volume ratio as the eluent.

Nuclear magnetic resonance spectra ($D_6$-DMSO)

| | |
|---|---|
| δ(p.p.m.): | 1.47 (9H, $(CH_3)_3COOC-$), |

-continued

| | |
|---|---|
| | 5.42 (1H, =C 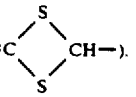 CH—). |

EXAMPLE 18

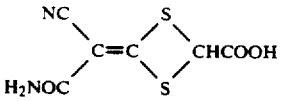

To 0.4 g. of tert-butyl 4-[(carbamoyl)(cyano)methylene]-1,3-dithietan-2-carboxylate obtained in Reference example 7 were added 2 ml. of anisole and 8 ml. of trifluoroacetic acid. And the mixture was stirred for one hour at room temperature. The solvents were distilled off under reduced pressure and the residue was mixed with 10 ml. of ether followed by stirring for one hour. The precipitates thus formed were recovered by filtration, washed with ether, and dried under reduced pressure to provide 0.15 g. of 4-[(carbamoyl)(cyano)methylene]-1,3-dithietane-2-carboxylic acid.

EXAMPLE 19

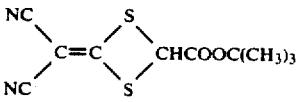

To 15 ml. of methylene chloride was added 0.28 g. of tert-butyl 4-[(carbamoyl)(cyano)methylene]-1,3-dithietane-2-carboxylate obtained in Example 17. After adding thereto 0.33 g. of pyridine and 0.43 g. of phosphorus pentachloride, the mixture was stirred for 30 minutes at room temperature. Then, 30 ml. of chloroform was added to the reaction mixture and the mixture was washed with 1 normal sulfuric acid, a 5% aqueous sodium carbonate solution, and then a saturated aqueous sodium chloride solution. The mixture was then dried over anhydrous magnesium sulfate and the solvent was distilled off under reduced pressure. The residue formed was subjected to a silica gel column chromatography to provide 0.23 g. of tert-butyl 4-dicyanomethylene-1,3-dithietan-2-carboxylate using chloroform as the eluent.

Nuclear magnetic resonance spectra ($CDCl_3$)

| | |
|---|---|
| δ(p.p.m.): | 1.54 (9H, $-COOC(CH_3)_3$)<br>5.02 (1H, =C 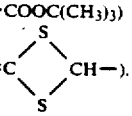 CH—). |

EXAMPLE 20

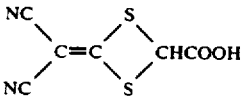

To 0.23 g. of tert-butyl 4-dicyanomethylene-1,3-dithietane-2-carboxylate obtained in Example 19 were added 2 ml. of anisole and 6 ml. of trifluoroacetic acid.

And the mixture was stirred for 3 hours at room temperature. The solvents were distilled off under reduced pressure and 10 ml. of hexane was mixed with the residue followed by stirring for 10 minutes. The solvent was removed by decantation. Then the same procedure was applied twice to the residue thus formed. The residue was then dried under reduced pressure to provide 0.18 g. of 4-dicyanomethylene-1,3-dithietane-2-carboxylic acid.

EXAMPLE 21

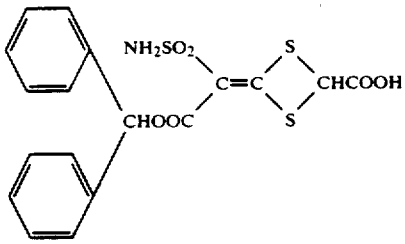

To 1.12 g. of benzhydryl sulfamoylacetate were added 30 ml. of anhydrous tetrahydrofuran and 20 ml. of tert-butanol.

After cooling the mixture to −20° C., 0.177 g. of sodium hydride (50% in oil) was added to the mixture followed by stirring for 15 minutes. To the mixture was added 0.3 g. of carbon disulfide. The mixture was stirred for 30 minutes at −10° C. to −5° C. Then, to the mixture were added 0.354 g. of sodium hydride (50% in oil) and 1.05 g. of diiodoacetic acid. After stirring the mixture for 20 minutes at −10° C. to 0° C., the mixture was stirred overnight at room temperature. The solvent was distilled off from the reaction mixture under reduced pressure and after adjusting the residue to pH 2 by adding thereto ice-water and 5% hydrochloric acid, the reaction mixture was extracted with ethyl acetate. The extract was washed twice, each time with a saturated aqueous sodium chloride solution, dried over anhydrous magnesium sulfate, and then the solvent was distilled under reduced pressure. The residue was subjected to a silica gel column chromatography to provide 0.2 g. of 4-[(benzhydryloxycarbonyl)(sulfamoyl)methylene]-1,3-dithietane-2-carboxylic acid using a mixture of chloroform and methanol of 10:1 by volume ratio as the eluent.

Nuclear magnetic resonance spectra ($CDCl_3$)

| | |
|---|---|
| δ(p.p.m.): | 4.66 (1H, =C 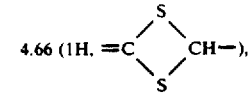 CH—), |
| | 6.96 (1H, $(C_6H_5)_2CH$—) |
| | 7.33 (10H, $(C_6H_5)_2CH$—). |

EXAMPLE 22

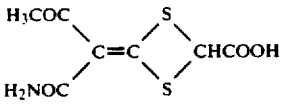

(a). In 50 ml. of tert-butanol was dissolved 5.76 g. of potassium tert-butylate and 50 ml. of anhydrous tetrahydrofuran was added to the solution. Then, after dissolving therein 2.6 g. of acetoacetamide, a solution prepared by dissolving 1.96 g. of carbon disulfide in 5 ml. of anhydrous tetrahydrofuran was added dropwise to the solution under ice-cooling. To the reaction mixture obtained was added 100 ml. of anhydrous tetrahydrofuran followed by stirring for 1.5 hours at room temperature. Then a suspension prepared by reacting 8 g. of diiodoacetic acid and 1.23 g. of sodium hydride (50% in oil) in 100 ml. of anhydrous tetrahydrofuran under ice-cooling was added to the mixture followed by stirring for 2.5 hours at room temperature.

The reaction mixture obtained was concentrated and the residue was mixed with 50 ml. of 1 normal hydrochloric acid and extracted with 100 ml. of ethyl acetate. The extract was washed with 50 ml. of an aqueous sodium chloride solution and the organic layer formed was extracted with 100 ml. of a saturated aqueous sodium hydrogencarbonate solution. The extract was adjusted to pH 2-3 with concentrated hydrochloric acid and then extracted with 100 ml. of ethyl acetate. The extract was washed with 50 ml. of an aqueous sodium chloride solution, dried over anhydrous magnesium sulfate, and concentrated.

The residue formed was dissolved in 30 ml. of methylene chloride and after adding thereto 5 g. of diphenyldiazomethane under ice-cooling, the mixture was stirred for 2 hours at room temperature. The reaction mixture was concentrated and the residue formed was subjected to a silica gel column chromatography to provide 0.6 g. of 4-[(acetyl)(carbamoyl)methylene]-1,3-dithietane-2-carboxylic acid benzhydryl ester using first chloroform and then a mixture of chloroform and methanol of 10:2 by volume ratio as the eluent.

Nuclear magnetic resonance spectra ($CDCl_3$)

| | |
|---|---|
| δ(p.p.m.): | 2.32 (3H, $H_3COC$—), |
| | 4.99 (1H, = 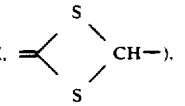 CH—), |
| | 6.97 (1H, —$COOCH(C_6H_5)_2$), |
| | 7.2-7.4 (10H, —$COOCH(C_6H_5)_2$). |

(b). In a mixture of 8 ml. of trifluoroacetic acid and 2 ml. of anisole was dissolved 0.6 g. of the product obtained in the step (a) at −20° C. and the temperature of the reaction mixture was raised to 10° C. over a period of 20 minutes. Then, the reaction mixture was concentrated and 10 ml. of a mixture of ether and petroleum ether of 1:1 by volume ratio was added to the residue to form precipitates, which were recovered by filtration to provide 0.2 g. of 4-[(acetyl)(carbamoyl)methylene]-1,3-dithietane-2-carboxylic acid.

Nuclear magnetic resonance spectra ($D_6$-DMSO)

| | |
|---|---|
| δ(p.p.m.): | 2.31 (3H, $H_3COC$—), |
| | 5.20 (1H, = 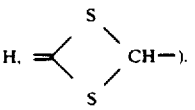 CH—). |

EXAMPLE 23

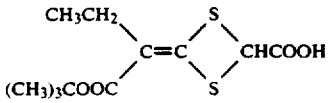

A mixture of 120 ml. of dimethoxyethane and 30 ml. of tetrahydrofuran was cooled to −74° C. in a dry ice-acetone bath and then 4.0 ml. of N-isopropylcyclohexylamine and then 13.72 ml. of a 15% n-butyl lithium n-hexane solution were added to the mixture, whereby the temperature raised from −73° C. to −62° C. After adding 3.17 g. of tert-butyl butylate and causing reaction for 30 minutes at −74° C. to −75° C., 0.664 ml. of carbon disulfide was added dropwise to the mixture over a period of 10 minutes followed by reaction for 20 minutes at the temperature. Then, 6.86 ml. of a 15% n-butyl lithium n-hexane solution was added dropwise to the reaction mixture at a temperature below −72° C. over a period of 10 minutes and then they were caused to react for 30 minutes. Then, 0.332 ml. of carbon disulfide was added to the reaction mixture over a period of 10 minutes and the reaction was performed for 20 minutes. Furthermore, 3.43 ml. of a 15% n-butyl lithium n-hexane solution was added dropwise to the reaction mixture at a temperature below −72° C. over a period of 13 minutes and then the reaction was further performed for 20 minutes at −74° C. to −73° C. Moreover, 0.166 ml. of carbon disulfide was added to the reaction mixture at about −74° C. over a period of 6 minutes and the reaction was performed for about 25 minutes. Thereafter, sodium diiodoacetate prepared by reacting 0.84 g. of 50% sodium hydride and 5.46 g. of diiodoacetate acid in 25 ml. of dimethoxyethane was added to the reaction mixture followed by reaction for 30 minutes at 0°-5° C. and then the reaction was further continued overnight at room temperature. The solvent was distilled off under reduced pressure from the reaction mixture and the residue was extracted with the addition of 50 ml. of cold ether and 40 ml. of 1 normal hydrochloric acid. The ether layer obtained was extracted twice, each time with 20 ml. of a saturated aqueous sodium hydrogencarbonate solution. The aqueous extracts were combined and adjusted to pH 1 with 1 normal hydrochloric acid, extracted twice with 30 ml. and 20 ml. of ether, successively. The extracts were combined and washed with water, dried over anhydrous magnesium sulfate, and then ether was distilled off to provide 1.08 g. of an oily product. The oily product was applied to a silica gel chromatographic column and the fractions containing the product were collected using a mixture of chloroform and methanol of 10:1 by volume ratio to provide 630 mg. of the brown oily 4-(1-carboxypropylidene)-1,3-dithietane-2-carboxylic acid.

Nuclear magnetic resonance spectra ($CDCl_3$)

| | |
|---|---|
| δ(p.p.m.): | 1.24 (3H, $-CH_3$, t), |
| | 1.47 (9H, $(CH_3)_3C-$, s), |
| | 2.01 (2H, $-CH_2-$, q), |
| | 4.87 (1H, 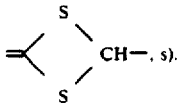 CH−, s). |

EXAMPLE 24

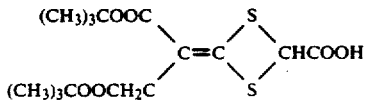

To a mixture of 80 ml. of diethylene glycol dimethyl ether and 20 ml. of tetrahydrofuran was added 1.54 ml. of diisopropylamine. And the mixture was cooled to −74° C. with dry ice-acetone bath. Then, 6.86 ml. of a 15% n-butyl lithium n-hexane solution was added to the mixture followed by reaction for 10 minutes at −72° C. to −74° C. Furthermore, 2.3 g. of tert-butyl succinate was added to the reaction mixture and the reaction was further carried out for 30 minutes at −74° C. Then, 0.332 ml. of carbon disulfide was added dropwise to the reaction mixture over a period of about 15 minutes and then the reaction was continued for 15 minutes at −74° C. Also, 3.43 ml. of a 15% n-butyl lithium n-hexane solution was added dropwise to the reaction mixture at a temperature below −71° C. over a period of 20 minutes and the reaction was carried out for 20 minutes at the same temperature. Thereafter, 0.166 ml. of carbon disulfide was added dropwise to the reaction mixture over a period of 13 minutes at a temperature below −72° C. and the reaction was carried out for 17 minutes at the temperature. Moreover, 1.715 ml. of a 15% n-butyl lithium n-hexane solution was added dropwise to the reaction mixture over a period of 10 minutes at a temperature below −71° C. Finally, 0.083 ml. of carbon disulfide was added dropwise to the reaction mixture over a period of 10 minutes and then the reaction was further carried out for 20 minutes at −72° C. to −74° C.

Separately, a suspension of sodium diiodoacetate prepared beforehand from 432 mg. of 50% sodium hydride and 2.8 g. of diiodoacetic acid in 20 ml. of diethylene glycol dimethyl ether dropwise to the reaction mixture obtained in the aforesaid reaction, whereby the temperature in the system raised from −74° C. to −64° C. Then, the temperature was allowed to raise and after carrying out the reaction for one hour at 0°-5° C., the mixture was stirred overnight at room temperature to cause further the reaction. Thereafter, the solvent was distilled off at room temperature under reduced pressure to provide a brown residue. The residue was mixed with 50 ml. of ether and 20 ml. of a cold 10% sulfuric acid and extracted with ether. The ether layer formed was extracted twice, each time with 50 ml. of a saturated sodium hydrogencarbonate solution. The aqueous layer obtained was mixed with 50 ml. of 10% sulfuric acid and extracted with 50 ml. and 30 ml. of ether, successively. The ether extracts were combined and washed twice, each time with 30 ml. of a saturated aqueous sodium chloride solution, dried over anhydrous magnesium sulfate, and ether was distilled off to provide 1.83 g. of an oily product. The oily product was applied to a silica gel chromatography column using 70 g. of silica gel, eluted using first chloroform and then a mixture of chloroform and methanol of 50:1 by volume ratio, and the fractions containing the product were collected to provide 700 mg. of 4-[1,2-bis(tert-butoxycarbonyl)]-1,3-dithietane-2-carboxylic acid.

Nuclear magnetic resonance spectra ($CDCl_3$)

| | |
|---|---|
| δ(p.p.m.): | 1.22 (18H, 2 × $(CH_3)_3C-$), 2.58 (2H, $-CH_2-$), 4.91 (1H, S/S CH—). |
| | Mass spectra: |
| m/e: | 362 $M^+$ |

What is claimed is:

[1. 7-substituted cephalosporin or penicillin derivatives represented by the formula

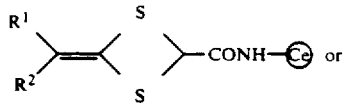

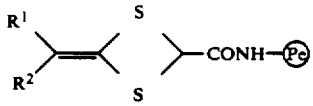

wherein $R^1$ is a carboxyl group or the functional derivative residue thereof selected from the group consisting of carboxylic acid lower alkyl ester residue, carboxylic acid aralkyl ester residue, a carbamoyl group, N-monoalkylcarbamoyl group, N,N-dialkylcarbamoyl group, a carboazoyl group, and a cyano group; $R^2$ is a carboxyl group or the functional derivative residue thereof selected from the group consisting of carboxylic acid lower alkyl ester residue, carboxylic acid aralkyl ester residue, a carbamoyl group, N-monoalkylcarbamoyl group, N,N-dialkylcarbamoyl group, a carboazoyl group, and a cyano group, a hydrogen atom, a lower alkyl group, a lower hydroxyalkyl group, a lower alkoxyalkyl group, a lower carboxyalkyl group, a lower arylalkyl group, a lower alkoxy group, a lower alkanoyl group, $R^4S(O)_n$ group wherein $R^4$ represents a lower alkyl group and n represents 0, 1 or 2, and aryl group which may have a substituted selected from the group consisting of hydroxyl and alkoxy groups, an aroyl group, a lower alkenyl group, a sulfamoyl group, or a heterocyclic residue which may have a substituent selected from the group consisting of a hydroxyl group, methyl group, and alkylthio group; and wherein Ce and Pe represent a cephalosporin nucleus and a penicillin nucleus, respectively.]

*2. 6-substituted penicillin derivative represented by the formula*

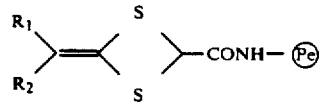

*wherein $R^1$ is a carboxyl group or the functional derivative residue thereof selected from the group consisting of carboxylic acid lower alkyl ester residue, carboxylic acid aralkyl ester residue, a carbamoyl group, N-monoalkylcarbamoyl group, N,N-dialkylcarbamoyl group, a carboazoyl group, and a cyano group; $R^2$ is a carboxyl group or the functional derivative residue thereof selected from the group consisting of carboxylic acid lower alkyl ester residue, carboxylic acid aralkyl ester residue, a carbamoyl group, N-monoalkylcarbamoyl group, N,N-dialkylcarbamoyl group, a carboazoyl group, and a cyano group, a hydrogen atom, a lower alkyl group, a lower hydroxyalkyl group, a lower alkoxyalkyl group, a lower carboxyalkyl group, a lower arylalkyl group, a lower alkoxy group, a lower alkanoyl group, $R^4S(O)_n$ group wherein $R^4$ represents a lower alkyl group and n represents 0, 1 or 2, and aryl group which may have a substituent selected from the group consisting of hydroxyl and alkoxy groups, an aroyl group, a lower alkenyl group, a sulfamoyl group, or a heterocyclic residue which may have a substituent selected from the group consisting of a hydroxyl group, methyl group, and alkylthio group; and wherein Pe represents a penicillin nucleus.*

*3. The 6-substituted penicillin derivative of claim 2 wherein $R_1$ and $R_2$ are each a carboxyl group.*

*4. The 6-substituted penicillin derivative of claim 2 wherein $R_1$ is a carboxyl group and $R_2$ is a lower alkylthio group.*

*5. The 6-substituted penicillin derivative of claim 2 wherein $R_1$ is a carboxyl group and $R_2$ is a lower alkoxy group.*

*6. The 6-substituted penicillin derivative of claim 2 wherein $R_1$ is a carboxyl group and $R_2$ is a lower alkyl group.*

*7. The 6-substituted penicillin derivative of claim 2 wherein $R_1$ is a carboxyl group and $R_2$ is hydrogen.*

*8. 7-substituted cephalosporin derivative represented by the formula*

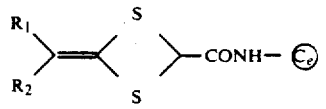

*wherein $R^1$ is an N-monoalkylcarbamoyl group or an N,N-dialkylcarbamoyl group; $R^2$ is a carboxyl group or the functional derivative residue thereof selected from the group consisting of carboxylic acid lower alkyl ester residue, carboxylic acid aralkyl ester residue, a carbamoyl group, N-monoalkylcarbamoyl group, N,N-dialkylcarbamoyl group, a carboazoyl group, and a cyano group, a hydrogen atom, a lower alkyl group, a lower hydroxyalkyl group, a lower alkoxyalkyl group, a lower carboxyalkyl group, a lower arylalkyl group, a lower alkoxy group, a lower alkanoyl group, $R^4S(O)_n$ group wherein $R^4$ represents a lower alkyl group and n represents 0, 1 or 2, and aryl group which may have a substituent selected from the group consisting of hydroxyl and alkoxy groups, an aroyl group, a lower alkenyl group, a sulfamoyl group, or a heterocyclic residue which may have a substituent selected from the group consisting of a hydroxyl group, methyl group, and alkylthio group; and wherein Ce represents a cephalosporin nucleus.*

* * * * *